United States Patent [19]

Palm

[11] Patent Number: 4,983,631

[45] Date of Patent: Jan. 8, 1991

[54] AGENT AND METHOD FOR EXTERNAL TREATMENT OF DOMESTIC ANIMALS

[76] Inventor: Roland Palm, Mobodarne 7861, S-826 00 Söderhamn, Sweden

[21] Appl. No.: 203,990

[22] PCT Filed: Nov. 16, 1987

[86] PCT No.: PCT/SE87/00536

§ 371 Date: Jun. 8, 1988

§ 102(e) Date: Jun. 8, 1988

[87] PCT Pub. No.: WO88/03794

PCT Pub. Date: Jun. 2, 1988

[30] Foreign Application Priority Data

Nov. 19, 1986 [SE] Sweden ................ 8604943

[51] Int. Cl.⁵ .............. A61K 31/23; A61K 31/19; A61K 31/20; A61K 31/125
[52] U.S. Cl. .................... 514/552; 514/557; 514/558; 514/692; 514/724
[58] Field of Search ............ 514/552, 558, 692, 557, 514/724

[56] References Cited

FOREIGN PATENT DOCUMENTS 120573 1/1948 Sweden .
144313 3/1954 Sweden .
168879 11/1934 Switzerland .
309012 4/1929 United Kingdom .

OTHER PUBLICATIONS

H. Enell, H. Thedenius, R. Luhr, Pharmaca Composita 2; a uppl., C & E Gernandts Förlags Aktiebolag, Stockholm 1896, pp. 218, 252, 405.
Ullmanns Encyklopädie der technischen Chemie, Dritte Auflage, 10.Band, pp. 683, 699.
R. E. Kirk & D. F. Othmer, Encyclopedia of Chemical Technology, vol. 4, pp. 500-551.
The Merck Index, Tenth Ed., pp. 1012-1013.

*Primary Examiner*—John W. Rollins
*Attorney, Agent, or Firm*—Shapiro and Shapiro

[57] ABSTRACT

The invention relates to an agent for treating the skin of domestic animals, consisting of a mixture of the following composition, expressed in per cent by volume:
15-30%: soft soap
4-10%: peanut oil
4-10%: spirit of camphor
1-5%: spirit of vinegar
30-50%: lower aliphatic alcohol
20-40%: water.

The invention also relates to a method for preparing such an agent by successively mixing the included components with each other at room temperature and in the order indicated above.

The invention further relates to the use of such an agent for skin-softening purposes. The agent is then applied to the udder and teats of cows.

8 Claims, No Drawings

AGENT AND METHOD FOR EXTERNAL TREATMENT OF DOMESTIC ANIMALS

FIELD OF THE INVENTION

The invention relates to an agent for treating the skin of domestic animals, especially cows, and in particular the udders and teats thereof.

BACKGROUND OF THE INVENTION

In order to meet the stringent standards applicable to products of today's sophisticated animal husbandry industry, and in order to maximize productivity, it is of the utmost importance that domestic animals be kept in good shape and that infections and injuries be avoided and prevented.

In the case of cows, there is a special problem resulting from the fact that the udders and the teats of the cows are subjected to heavy strains and that these zones thus easily become swollen and infected. This, in turn, may affect the milk produced which may be contaminated with bacteria and thus declared unfit. Even if there are medicines for curing such diseases relatively quickly, the loss of milk production may nonetheless become significant since, during an infection and some time after it, the cow must go dry. It is therefore desirable to take steps to avoid and prevent the occurrence of such injuries and infections.

Hitherto, several different preparations have been used for different situations in connection with the treatment of the udders of milking cows, such as a disinfectant for destroying bacteria, an ointment for treating swellings and an ointment for treating chapping and wounds. These ointments are however relatively difficult to apply, however, and also often leave a smeary surface.

DESCRIPTION OF THE INVENTION

The present invention relates to an agent for treating the skin of domestic animals, especially cows, both for prophylactic reasons and as a continuous cure. The invented agent is in the form of a homogeneous liquid of the following composition, expressed in percent by volume:
15–30%: soft soap
4–10%: peanut oil
4–10%: spirit of camphor
1–5%: spirit of vinegar
30–50%: lower aliphatic alcohol
20–40%: water.

The term "soft soap" as used in this context relates to ordinary commercial yellow soap substantially containing tall oil, fatty acids and caustic soda. The term "lower aliphatic alcohol" relates to an alcohol having 1–10 carbon atoms, preferably 1–6 carbon atoms, especially monoalcohols, with special preference for isopropanol. The term "spirit of camphor" relates to an at least 20% solution of camphor in alcohol, which alcohol preferably is the same as the alcohol included in the composition.

In previously known compositions intended to be applied to the skin of humans or animals, lower alcohols in the form of solvents are a commonly used component, as are different oils and fats used as consistency and softening agents. Further, camphor is a known constituent in liniments and thus known in skin-treating contexts. Soap of different kinds has hitherto been used in compositions to be applied to the skin, but there is no prior disclosure of the use of common commercial soft soap.

For the use of soft soap and alcohol, see CH-A 168,879; for the use of spirit of vinegar and alcohol, see H. Enell, H. Thedenius and R. Luhr, Pharmaca Composita, second edition, C & E Gernandts Forlags Aktiebolag, Stockholm 1896, pp. 218 and 405; for the use of peanut oil, see Ullmanns Encyklopädie der technischen Chemie, dritte Auflage, 10. Band, pp. 683 and 693; and for the use of camphor, see SE-A 120,573.

A composition consisting of the majority or all of the components included in the agent of the present invention was not previously known. Thus, the invention provides a new agent which has been found to produce an effect which was not foreseeable on the basis of the individual components included, which when used together in the agent of the invention have proved to coact in a manner to produce an unexpected and valuable effect.

The agent of the present invention is intended for external application to domestic animals, especially cows, and serves both to destroy bacteria and to soften the skin. When the agent is applied to the udder and teats of cows, the blood circulation through these parts increases, so that swellings are caused to disappear and the skin is softened. An efficient way of treating a cow with the agent of the present invention is, after each milking event, to apply the agent, e.g. by means of a spray device, to the teats and, if required, also to the udders of the cow. In this manner, it is possible to counteract and prevent the occurrence of swellings, skin trouble and infections, and thus to considerably facilitate the milking operation and improve the conditions for a reduced cell content, i.e. a low bacteria count, in the milk.

The present agent can also be used for treating domestic animals other than cows in cases where the skin of the animals is subjected to strains of different kinds.

The agent according to the invention has a preferred composition as indicated below, expressed in percent by volume:
18–25%: soft soap
5–8%: peanut oil
5–8%: spirit of camphor
1.5–3%: spirit of vinegar
35–45%: lower aliphatic alcohol
22–30%: water.

A particularly preferred embodiment of the invention has the following composition:
20%: soft soap
6%: peanut oil
6%: spirit of camphor
2%: spirit of vinegar
40%: isopropanol
26%: water.

The agent according to the invention is prepared by successively mixing the components with each other at room temperature and in a certain, suitable order as stated in Example 1 below.

The functions of the different components of the composition have been studied by successively excluding each one of the components. The following conclusions have been drawn:

(a) Soft soap — This component has both a cleansing effect and a swelling-reducing and swelling-inhibiting effect by increasing blood circulation.

(b) Peanut oil — This component both gives the composition a suitable consistency and has an emollient and protective effect. Without this component, the other relatively aggressive components of the agent would tend to burn the teats of the treated animal.

(c) Spirit of camphor — This component has a swelling-reducing and swelling-inhibiting effect, but also makes the composition coherent and adherent. When spraying an agent without any spirit of camphor included, the agent will soon trickle off the udder and drop onto the ground, whereas an agent containing spirit of camphor will adherently flow along the surface of the udder.

(d) Alcohol — This component has a bactericidal effect.

(e) Water — is used in suitable amounts to avoid having an excessive percent by volume of alcohol.

f) Spirit of vinegar — This component also has a bactericidal effect, but additionally seems to interact synergistically with the other components, strengthening their effect. In tests without spirit of vinegar included, none of the surprisingly good effects regarding skin softening and swelling reduction as otherwise found when using the agent were achieved to any noticeable extent.

The agent according to the invention also means a considerable simplification for the treatment and cure of the udders of milking cows. Hitherto, it has been necessary to use several different preparations for different situations, such as one ointment for swellings, one ointment for wounds and chapping, and one preparation (of iodine) for destroying bacteria and obturating the teat canals for avoiding infections. With the invention, all these functions are obtained in one and the same preparation which, moreover, is easier to apply, since it is in spray form and is rapidly absorbed into the skin and leaves no smeary layer as in the case of ointments.

It may also be pointed out that the present agent has met with substantial success for preventing and palliating so-called summer sores. This is a disease afflicting summer cows with sensitive udders when in open pasture where the sun, in combination with dirt and mud which have clogged to the cow's skin, may cause injuries to the udders and the teats.

The invented agent has been tested for six months on stock within a certain geographical area of Sweden. Very good results have been obtained as regards reduction of udder swellings in cows and, in sensitive cows, also inhibition of such swellings, as well as softening of the skin of the teats. Cows continuously treated with the agent have thus exhibited healthy udders and teats, have been easy to milk and have yielded milk with low cell content. The agent has also been tested on horses in some contexts where the skin has been subjected to strains, and good results have also been obtained in these cases. Further, tests have been carried out, excluding certain components in the composition or replacing them with similar components, as reported in Examples 2 and 3 below. In these cases, a dramatically reduced effect, or almost no effect at all, was obtained. The agent according to the invention thus has a unique composition where the included components interact in an unexpected synergistic manner, producing a valuable effect.

EXAMPLE 1

A batch of 5 l of the agent was prepared in the following way:

10 dl of soft soap was admixed with 3 dl of peanut oil. 3 dl of spirit of camphor of a previously prepared solution, obtained by dissolving 1.5 kg of camphor in a small amount of isopropanol and diluting it with isopropanol to give a 20% solution, was then added. To the resultant mixture was then added 1 dl of spirit of vinegar, whereupon 2 l of isopropanol was admixed and the mixture diluted with 1.3 l of water.

The thus prepared composition was then placed in a spray device. The composition can be sprayed onto the teats of a cow after milking. If the udder of the cow seems strained, the composition can also be sprayed onto it after each milking event. If the udder is healthy, it is sufficient to spray it from 1-2 times a week up to once a day.

EXAMPLE 2

A batch of the agent was prepared in the same manner as in Example 1, but without spirit of vinegar.

When using the agent on cows according to Example 1, practically none of the skin-softening and blood circulation-promoting effects obtained with the agent according to the invention were observed, and swellings on the cows were not appreciably affected.

EXAMPLE 3

A batch of the agent was prepared in the same manner as in Example 1, but replacing the soft soap with tall oil.

When using the agent on cows according to Example 1, an approximately equally low effect was obtained as in Example 2.

I claim:

1. An agent for treating the skin of domestic animals, which, on a percent by volume basis, consists essentially of the following ingredients:
   15–30%: soft soap
   4–10%: peanut oil
   4–10%: spirit of camphor
   1–5%: spirit of vinegar
   30–50%: lower aliphatic alcohol
   20–40%: water.

2. An agent as claimed in claim 1, wherein the ingredients are present in the following amounts on a percent by volume basis:
   18–25%: soft soap
   5–8%: peanut oil
   5–8%: spirit of camphor
   1.5–3%: spirit of vinegar
   35–45%: lower aliphatic alcohol
   22–30%: water.

3. An agent as claimed in claim 1, wherein said lower aliphatic alcohol is isopropanol and the ingredients are present in the following amounts on a percent by volume basis:
   20%: soft soap
   6%: peanut oil
   6%: spirit of camphor
   2%: spirit of vinegar
   40%: isopropanol
   26%: water.

4. A method of treating the skin of domestic animals for purposes including softening, swelling prevention, and curing of swellings, infections, chapping, and wounds, said method comprising applying to the skin an agent which, on a percent by volume basis, consists essentially of:
   15–30%: soft soap 4–10%: peanut oil
4–10%: spirit of camphor
1–5%: spirit of vinegar
30–50%: lower aliphatic alcohol
20–40%: water.

5. A method of treating skin disorders of the udders and teats of cows, including swellings, infections, chapping, and wounds, said method comprising applying to the udders and teats an agent which, on a percent by volume basis, consists essentially of:

15–30%: soft soap
4–10%: peanut oil
4–10%: spirit of camphor
1–5%: spirit of vinegar
30–50%: lower aliphatic alcohol
20–40%: water.

6. A method as claimed in claim 5, wherein the agent is applied by spraying.

7. A method for treating healthy udders and teats of cows for purposes of softening and swelling-prevention, comprising applying to the udders and teats an agent which, on a percent by volume basis, consists essentially of:

15–30%: soft soap
4–10%: peanut oil
4–10%: spirit of camphor
1–5%: spirit of vinegar
30–50%: lower aliphatic alcohol
20–40%: water.

and repeating the application at intervals sufficient to maintain softness and prevent substantial swelling.

8. A method as claimed in claim 7, wherein the agent is applied by spraying.

* * * * *